United States Patent [19]

Haas et al.

[11] Patent Number: 5,426,249

[45] Date of Patent: Jun. 20, 1995

[54] PROCESS FOR THE SIMULTANEOUS PRODUCTION OF 1,2- AND 1,3-PROPANEDIOL

[75] Inventors: Thomas Haas, Frankfurt; Armin Neher, Brachttal; Dietrich Arntz, Oberursel; Herbert Klenk; Walter Girke, both of Hanau, all of Germany

[73] Assignee: Degussa Akteingesellschaft, Frankfurt, Germany

[21] Appl. No.: 151,389

[22] Filed: Nov. 12, 1993

[30] Foreign Application Priority Data

Nov. 14, 1992 [DE] Germany .......... 42 38 492.3

[51] Int. Cl.$^6$ .......... C07C 31/20; C07C 29/141; C07C 29/145
[52] U.S. Cl. .......... 568/862; 568/403; 568/486
[58] Field of Search .......... 568/862, 486, 403

[56] References Cited

U.S. PATENT DOCUMENTS

| | | | |
|---|---|---|---|
| 2,042,224 | 5/1936 | Groll et al. | 260/138 |
| 2,558,520 | 6/1951 | Hoyt et al. | 260/603 |
| 4,642,394 | 2/1987 | Che | 568/861 |
| 5,015,789 | 5/1991 | Arntz et al. | 568/862 |
| 5,171,898 | 12/1992 | Arntz et al. | 568/862 |
| 5,210,335 | 5/1993 | Schuster et al. | 568/863 |
| 5,274,187 | 12/1993 | Kimura et al. | 568/471 |

FOREIGN PATENT DOCUMENTS

| | | |
|---|---|---|
| 0487903 | 7/1992 | European Pat. Off. . |
| 695931 | 12/1930 | France . |
| 888096 | 8/1953 | Germany . |
| 3926136 | 2/1991 | Germany . |
| 4138981 | 11/1991 | Germany . |
| 4138982 | 11/1991 | Germany . |
| 4218282 | 11/1991 | Germany . |
| 4038192 | 6/1992 | Germany . |

OTHER PUBLICATIONS

Chem. Abstr. 99(13): 103663s (Environ. Microbiol. (1983), vol. 46(1), pp. 62–67).

Koichi, I., et al., "Generation of trance amount of acrolein standard gas chromatogrphy", Bunseki Kagaku (1983), vol. 32 pp. E321–E325.

Studies in surfaces science and catalysis, vol. 51, 1989: "New solid acids and bases, their catalytic properties" by K. Tanabe et al., Chapter 1 (pp. 1–3) and Chapter 2 (pp. 5 to 9).

Guenzel, B., "Fermentative production of 1,3--propanediol from glycerol by Clostridium butyricum up to a scale of 2 m$^3$", Appl. Microbiol. Biotechnol. (1991), vol. 36, pp. 289–294.

Ser. No. 07/980,995 date Nov. 24, 1992 Haas et al.
Ser. No. 07/981,324 date Nov. 24, 1992 Haas et al.
Ser. No. 08/063,317 date May 19, 1993 Haas et al.

*Primary Examiner*—Johann Richter
*Assistant Examiner*—Rebecca Cook
*Attorney, Agent, or Firm*—Beveridge, DeGrandi, Weilacher & Young

[57] ABSTRACT

A process is described for the simultaneous production of 1,2- and 1,3-propanediol from glycerol. The process involves the reaction stages (a) dehydration of glycerol by feeding a gaseous glycerol-water mixture with 10 to 40 wt % glycerol at 250° to 340° C. over a solid catalyst with an $H_0$ value (Hammett acidity function) of less than 2, preferably between $-3$ and $-8.2$, (b) hydration of the acrolein contained in the reaction mixture of stage (a), and (c) catalytic hydrogenation of the reaction mixture, containing 3-hydroxypropionaldehyde and hydroxyacetone, of stage (b). Two valuable products, namely 1,2- and 1,3-propanediol, can be obtained simultaneously and in high total yield from glycerol in a simple process.

14 Claims, No Drawings

PROCESS FOR THE SIMULTANEOUS PRODUCTION OF 1,2- AND 1,3-PROPANEDIOL

INTRODUCTION AND BACKGROUND

The present invention relates to a process for the simultaneous production of 1,2- and 1,3-propanediol from one raw material, namely glycerol, wherein the first step is a dehydration of glycerol.

1,2-propanediol is a commercially produced product with a broad spectrum of applications and 1,3-propanediol is gaining importance as a structural unit for polyesters. Various processes are known for the production of 1,2- and 1,3-propanediol. 1,2-propanediol is obtained for example by hydrolysis of propylene oxide. 1,3-propanediol is obtained in general by hydration of acrolein on an acidic catalyst to produce 3-hydroxypropionaldehyde and then catalytic hydration of the 3-hydroxypropionaldehyde. With regard to the production of 1,3-propanediol from acrolein, reference is made for example to the processes described in the following documents: DE-A 39 26 136, DE-A 40 38 192, and German Patent Applications P 41 38 982.4, P 42 18 282.4 and P 41 38 981.6.

Only a few processes have become known whereby 1,2- and 1,3-propanediol are produced simultaneously from one raw material: 1,3- and 1,2-propanediol can be produced by reaction of glycerol with carbon monoxide and hydrogen in an organic solvent in the presence of a homogeneous catalyst system consisting of, for example, tungstic acid and a rhodium compound (see U.S. Pat. No. 4,642,394). A disadvantage of this process is the low yields of 1,2- and 1,3-propanediol, which in each case scarcely exceeds 20%; moreover, glycerol must be reacted in solution in an amine or amide, so that aqueous glycerol solutions cannot be used.

1,3-propanediol can be produced by fermentation from glycerol by *Clostridium butyricum* (see B. Günzel et al., Applied Microbiology and Biotechnology, Springer Verlag 1991, pages 289–294). Although this method leads to 1,3-propanediol in moderate yields (ca. 60%), it must not be disregarded that the space-time yield of 1,3-propanediol in this fermentation is very low, namely 2.3 to 2.9 $g \cdot l^{-1} \cdot h^{-1}$. The concentration of glycerol (about 5 to 6 g/l) in the solution to be fermented must be kept low since otherwise the growth of the cultures used is inhibited; the recovery of the 1,3-propanediol from the very dilute fermentation solutions is therefore energy-intensive. 1,2-propanediol is not formed.

According to another microbiological process (Environ. Microbiol. (1983), volume 46 (1), pages 62–67; Chem. Abstr. 99 (13): 103663s), glycerol can be converted by means of *Klebsiella pneumoniae* NRRL B-199 in 55% yield to 3-hydroxypropionaldehyde, the hydration product of acrolein, which can be converted in a known way to 1,3-propanediol. The fermentation is carried out using about 3% glycerol solutions and requires the presence of semicarbazide hydrochloride, which must be recovered again. The space-time yield of this process is low; moreover, the total process cost is high. Apparently no hydroxyacetone, which could be converted into 1,2-propanediol, is formed.

The formation of acrolein from glycerol, for example, has been studied in the gas phase under conditions of destructive gas chromatography (Ishikawa Koichi et al., Bunseki Kagaku 32 (10) E 321–E 325), wherein a very dilute aqueous solution of glycerol (1.5–150 mg/l) is fed at 260° to 300° C. in pulsed form over a gas chromatography (Poropak R) column coated with 10 to 30% $KHSO_4$. A man skilled in the art receives no inducement from this document to turn the analytical method into the basis of a manufacturing process for the production of 1,2- and 1,3-propanediol from glycerol since only acrolein is named as a dehydration product and, moreover, the extreme dilution creates conditions which are completely different from those necessary in manufacturing processes in order to achieve a satisfactory space-time yield and catalyst life.

A process for the production of acrolein from glycerol is known from FR 695 931, wherein glycerol vapor is fed at above 300° C., especially 400° to 420° C., over a fixed-bed catalyst. Salts of tribasic acids or mixtures of such salts, which can be present on a support, are claimed as catalyst; as shown in the examples, pumice coated with 1% lithium phosphate or with 1% iron phosphate is used. In this document, as shown in the examples, the acrolein yield is reported to be 75% or 80%. Advice to use the reaction mixture of the dehydration for the production of 1,2- and 1,3-propanediol cannot be found in this document. We have duplicated the process of FR 695 931 and in doing so established that under the reaction conditions tested the reported yields could not be obtained either with lithium phosphate or with iron phosphate; as the comparative examples show, the yield of acrolein at 300° C. was only about 1 to 3% and at 400° C. was 30 to 35%.

SUMMARY OF THE INVENTION

An object of the present invention is to provide a manufacturing process for the simultaneous production of 1,2- and 1,3-propanediol from glycerol, which is non-fermentative, and permits the propanediols to be produced in higher total yield than was possible in the previously known processes. In addition, the use of organic solvents is to be avoided.

In achieving the above and other objects, one feature of the present invention resides in a process comprising the following reaction stages:

(a) dehydration of glycerol with formation of an aqueous solution containing acrolein and hydroxyacetone by feeding a glycerol-water mixture, with a glycerol content of 10 to 40 wt %, in the gas phase at 250° to 340° C. over an acidic solid catalyst with an $H_0$ value (Hammett acidity function) of less than +2 and condensing the gaseous product stream to the aqueous solution mentioned;

(b) hydration of the acrolein contained in the condensed product stream to 3-hydroxypropionaldehyde by treatment of the condensed product stream of stage (a) in a known manner at 20° to 120° C. in the presence of a conventional acidic hydration catalyst; and (c) catalytic hydrogenation of the 3-hydroxypropionaldehyde and hydroxyacetone contained in the aqueous reaction solution of stage (b) to 1,3- and 1,2-propanediol by freeing the reaction solution of stage (b) from unreacted acrolein and subsequently hydrogenating the reaction solution in a known manner, using conventional hydrogenation catalysts, and separating the reaction mixture of stage (c) by distillation.

DETAILED DESCRIPTION OF THE INVENTION

U.S. Pat. Nos. 5,015,789; 5,171,898; 5,276,201; 5,334,778; and 5,364,984 are incorporated by reference in their entirety.

It has been found that during the dehydration of glycerol under the conditions according to reaction stage (a) herein, acrolein and hydroxyacetone are formed. According to the present invention, the product stream of stage (a) without previous purification is subjected in reaction stage (b) to conditions under which acrolein is converted in aqueous phase in a manner known in the art to 3-hydroxypropionaldehyde. The product stream of stage (b), which contains 3-hydroxypropionaldehyde and hydroxyacetone, is fed, after topping or distilling off unreacted acrolein, to the hydrogenation stage, wherein the aforementioned carbonyl compounds are hydrogenated under conventional conditions (such as are known in particular from the hydrogenation of 3-hydroxypropionaldehyde to 1,3-propanediol) to 1,3- and 1,2-propanediol.

It could not have been foreseen that 1,2- and 1,3-propanediol could be obtained simultaneously from glycerol with a good total yield. Moreover, it was surprising that it was possible not to separate the two valuable products from each other until after the third reaction stage; consequently, no intermediate purification of the product stream in stage (a) and stage (b) is required except for the separation of the possibly unreacted acrolein before stage (c). Finally, it was not to be expected in view of the prior art that an organic solvent was not necessary, but rather that an aqueous glycerol solution could be used as starting material.

It is essential for the present invention that an aqueous glycerol solution with a concentration of between 10 and 40 wt %, preferably between 10 and 25 wt %, be passed over the solid dehydration catalyst. Thus so-called crude glycerols from fat cleavage can be used, without the glycerol having to be first concentrated and purified. When a glycerol solution with a content of above 40 wt % is used, dehydration certainly still occurs but with increasing glycerol concentration both the selectivity of the reaction and the life of the catalyst fall markedly; the falling selectivity becomes apparent in particular through an increasing content of high-boiling point components. Aqueous glycerol with a concentration below 10 wt % can be used but the profitability of the process is reduced with falling concentration since the space-time yield falls and the expenditure of energy during the splitting-up by distillation of the reaction mixture of stage (c) rises.

The reaction of the glycerol in the gas phase leads, in general, to a glycerol conversion of practically 100% and, under the conditions described herein, to a high selectivity with respect to the formation of acrolein and hydroxyacetone. The gaseous reaction mixture leaving the catalyst (=product stream), which contains acrolein, hydroxyacetone and by-products, is immediately condensed and fed to the next stage.

Solid substances of single or multiphase structure, essentially stable under the reaction conditions and with an $H_0$ value of less than $+2$, preferably less than $-3$, are used as acidic solid catalysts. The $H_0$ function corresponds to the Hammett acidity function and can be easily determined by the well known so-called amine titration using indicators or by adsorption of a gaseous base (see Studies in surface science and catalysis, Vol. 51, 1989: "New solid acids and bases, their catalytic properties" by K. Tanabe et al., Chapter 2, in particular pages 5 to 9). Chapter 1 of the aforementioned document mentions on pages 1 to 3 numerous solid acids from which the man skilled in the art, optionally after determining the $H_0$ value, can select as the suitable catalyst. Suitable as solid catalysts for the dehydration are, for example: (i) natural and synthetic siliceous materials, and in particular mordenite, montmorillonite and acidic zeolites; (ii) carriers, such as oxidic or siliceous materials, for example $Al_2O_3$ or $TiO_2$, coated with mono-, di-, or polybasic inorganic acids, especially phosphoric acid, or with acid salts of inorganic acids; and (iii) oxides and mixed oxides, as for example gamma-$Al_2O_3$ and $ZnO$-$Al_2O_3$ mixed oxides or heteropolyacids. Such catalysts are well known in the art for these reactions.

For the dehydration in the gas phase, catalysts with an $H_0$ value of between $-3$ and $-8.2$ are especially preferred; these include $H_3PO_4$ on $Al_2O_3$ (so-called solid phosphoric acid). Catalysts of the type of zeolite H-ZSM5 are less suitable for the gas phase dehydration owing to their $H_0$ value of less than $-8.2$.

The production of the catalysts of type (ii) above is particularly simple: the support material is treated with an aqueous solution of the acid and the solid so treated is dried.

Glycerol is dehydrated in the gas phase at 250° to 340° C., preferably in the temperature range above 270° to 320° C. An increase of the temperature to above 340° C. causes a definite reduction of the selectivity. It has surprisingly been found that by a limitation of the temperature in the dehydration stage to a maximum of 340° C. and preferably 320° C., the life of the catalysts is so increased that they can be used in continuous operation on a commercial scale.

Reaction stage (a) according to the present invention can be carried out in conventional apparatuses, familiar to the man skilled in the art, for gas phase reactions on a solid catalyst. Such an apparatus comprises essentially a vaporizer for the glycerol-water mixture, the reactor in which the catalyst is as a rule arranged in the form of a fixed bed, and the heating devices for one or more temperature zones, as well as a device for condensation of the gaseous product stream.

It was certainly known that glycerol can be dehydrated in the gas phase in the presence of solid acidic catalysts with formation of acrolein, but it only became possible as a result of the conditions described herein to carry out the reaction stage (a) in such a way that it surprisingly resulted in a high total yield of both required dehydration products, a high space-time yield, and a good catalyst life.

Reaction stage (b) of the process according to the present invention is carried out in the same way as is known from processes for the hydration of acrolein in aqueous solution. The sole difference from the known processes for the production of 3-hydroxypropionaldehyde from acrolein is that the aqueous acrolein solution to be used is the condensed reaction mixture of stage (a) which additionally contains hydroxyacetone. The hydration is carried out in the presence of an acidic catalyst, either (1) in homogeneous phase, for example by means of an acid-base buffer at pH 3 to 4.5 according to DE Patent Application P 41 38 981.6 (corresponding to U.S. Pat. No. 5,284,979), or (2) in heterogeneous phase, for example by means of a cation exchanger with chelating active groups according to DE-A 39 26 136 (corresponding to U.S. Pat. No. 5,015,789) or DE-A 40 38 192 (corresponding to U.S. Pat. No. 5,171,898) or by means of a supported acid according to DE Patent Application P 41 38 982.4 (corresponding to U.S. Pat. No. 5,276,201), preferably at a temperature in the range from 50° to 90° C. and a pressure of 1 to 20 bar. Following the hydration, unreacted acrolein is removed from the reaction mixture, for example by stripping or distilling off, and the acrolein is fed back to the hydration. Additionally, a part of the water present can, if desired, be distilled out of the reaction mixture of stage (b) during or after the removal of acrolein.

The reaction mixture of stage (b), from which acrolein has been removed, is hydrogenated with hydrogen in reaction stage (c) in a manner known in the art for ketones and aldehydes using known hydrogenation catalysts. Hydrogenation is preferably carried out in the presence of a fixed bed or suspended catalyst at 5 to 300 bar, a pH value of 2.5 to 6.5 and a temperature of 30° to 180° C.; it is particularly expedient to carry out the hydrogenation according to DE Patent Application P 42 18 282.4 (corresponding to U.S. Pat. No. 5,334,778), first at 30° to 80° C. and then at 100° to 180° C. Known catalysts which may be used include those mentioned for example in U.S. Pat. No. 2,434,110 (incorporated by reference in its entirety), DE-OS 39 26 136 (corresponding to U.S. Pat. No. 5,015,789) and DE-OS 40 38 192 (corresponding to U.S. Pat. No. 5,171,898). Catalysts from the following group are preferred:

(i) Raney nickel which can also be doped with other metals effective for hydrogenation provided that it is exclusively a matter of a suspension hydrogenation;

(ii) supported catalysts based on platinum- or ruthenium-coated activated carbon or metal oxides, such as in particular $Al_2O_3$, $SiO_2$ or $TiO_2$; or (iii) nickel-coated oxidic or siliceous supported catalysts, preferably catalysts based on $Ni/Al_2O_3/SiO_2$.

Advantages of the process according to the present invention surprising include the following: two valuable products, namely 1,2- and 1,3-propanediol (PD), are accessible simultaneously in high total yield from glycerol; the usability of so-called crude glycerol with a content of 15 to 30 wt % reduces the raw material costs; the process can be operated with high selectivity and high space-time yield; and no organic solvents are required.

EXAMPLE 100 g Rosenthal beads ($Al_2O_3$) with a diameter of 3 mm are mixed with 25 g of a 20 wt % phosphoric acid for one hour. The excess water is removed on a rotary evaporator at 80° C. 100 ml of this catalyst are poured into a steel tube of 15 mm diameter. A 20 wt % aqueous glycerol solution is fed at 40 ml/h via a pump into an evaporator heated to 300° C. and the gas stream fed directly over the catalyst at 300° C. With quantitative glycerol conversion there is obtained in the condensed product stream a yield of 70.5% acrolein and ca. 10% hydroxyacetone, each relative to glycerol.

The resulting gaseous reaction mixture is then condensed. For hydration of the acrolein to 3-hydroxypropionaldehyde, the condensed product stream of stage (a) is reacted according to DE-A 40 38 192 (corresponding to U.S. Pat. No. 5,171,898) on an ion exchanger with iminodiacetic acid active groups (Lewatit TP 208, Bayer AG). The unreacted acrolein of stage (b) is separated by distillation from the product mixture as a 96% azeotrope with $H_2O$ and fed to the product stream from stage (a). Under stationary conditions an initial acrolein concentration of 14.3% is obtained; reaction temperature 50° C. LHSV=0.5 $h^{-1}$; conversion=60%, selectivity=85%.

The reaction mixture of stage (b), freed from unreacted acrolein, is hydrogenated according to DE Patent Application P 42 18 282.4 (corresponding to U.S. Pat. No. 5,334,778). Hydrogenation conditions: fixed-bed catalyst of $Ni/Al_2O_3/SiO_2$; temperature of the first stage 40° C. and of the second stage 140° C.; $H_2$ pressure 40 bar; LHSV 1 $h^{-1}$. The hydrogenated reaction mixture contains 9.9 wt % 1,3-propanediol and 1.6 wt % 1,2-propanediol. The mixture is worked up by distillation: boiling points at 50 mbar 109° C. for 1,2-PD and 134° C. for 1,3-PD. The product quality of the 1,2- and 1,3-propanediol corresponds to that which is well known from products usual in the market. Yield of 1,3-PD relative to glycerol used, 60%; yield of 1,2-PD, 10%.

Further variations and modifications of the foregoing will be apparent to those skilled in the art and such variations and modifications are attended to be encompassed by the claims that are appended hereto.

What is claimed:

1. A process for the simultaneous production of 1,2- and 1,3-propanediol from glycerol, said method comprising:

(a) dehydrating glycerol with formation of an aqueous solution containing acrolein and hydroxyacetone by feeding a glycerol-water mixture with a glycerol content of 10 to 40 wt % in the gas phase at 250° to 340° C. over an acidic solid catalyst with an $H_0$ value (Hammett acidity function) of less than +2 and condensing the gaseous product stream to the aqueous solution mentioned;

(b) hydrating the acrolein contained in the condensed product stream to 3-hydroxypropionaldehyde by treating the condensed product stream of stage (a) at 20° to 120° C. in the presence of an acidic hydration catalyst; and (c) catalytically hydrogenating the 3-hydroxypropionaldehyde and hydroxyacetone contained in the aqueous reaction solution of stage (b) to 1,3- and 1,2-propanediol by freeing the reaction solution of stage (b) from unreacted acrolein and subsequently hydrogenating the reaction solution using a hydrogenation catalyst and separating the reaction mixture of stage (c) into 1,2- and 1,3-propanediol by distillation.

2. The process according to claim 1 wherein step (a) is carried out at 270° to 320° C.

3. The process according to claim 1, wherein said acidic solid catalyst has an $H_0$ value between −3 and −8.2.

4. The process according to claim 1, wherein said glycerol-water mixture has a glycerol content of 10 to 25 wt %.

5. The process according to claim 1, wherein said acidic solid catalyst is a mordenite, montmorillonite or acidic zeolite.

6. The process according to claim 1, wherein said acidic solid catalyst is a oxidic or siliceous carrier coated with mono-, di-, or polybasic inorganic acids or with acid salts of inorganic acids 7. The process according to claim 6, wherein said carrier is $Al_2O_3$ or $TiO_2$ coated with phosphoric acid.

8. The process according to claim 1, wherein said acidic solid catalyst is an oxide, mixed oxide or heteropolyacid.

9. The process according to claim 8, wherein said acidic solid catalyst is gamma-$Al_2O_3$ or $ZnO$-$Al_2O_3$.

10. The process according to claim 1, wherein stage (c) is conducted (1) at 5 to 300 bar, a pH value of 2.5 to 6.5 and a temperature of 30° to 180° C. or (2) first at 30° to 80° C. and then at 100° to 180° C.

11. The process according to claim 1, wherein said stage (b) is conducted at a temperature in the range from 50° to 90° C. and a pressure of 1 to 20 bar.

12. The process according to claim 1, wherein said glycerol-water mixture has a glycerol content of 15 to 30 wt %.

13. The process according to claim 1, wherein said process does not involve the use of an organic solvent.

14. The process according to claim 1, wherein the yield of said 1,3-propanediol relative to said glycerol is at least 60% and the yield of said 1,2-propanediol relative to said glycerol is at least 10%.

* * * * *

UNITED STATES PATENT AND TRADEMARK OFFICE
CERTIFICATE OF CORRECTION

PATENT NO. : 5,426,249
DATED : June 20, 1995
INVENTOR(S) : Thomas Haas et al

It is certified that error appears in the above-indentified patent and that said Letters Patent is hereby corrected as shown below:

On title page, Assignee should read as follows:

Item [73] Degussa Aktiengesellschaft

Signed and Sealed this

Nineteenth Day of September, 1995

Attest:

BRUCE LEHMAN

*Attesting Officer*   *Commissioner of Patents and Trademarks*